United States Patent [19]

Bitsch

[11] Patent Number: 5,236,848
[45] Date of Patent: Aug. 17, 1993

[54] PROCEDURE AND AGENT FOR THE DETERMINATION OF NITRATE IONS

[75] Inventor: Roland Bitsch, Pfungstadt, Fed. Rep. of Germany

[73] Assignee: Merck Patent Gesellschaft mit Beschrankter Haftung, Darmstadt, Fed. Rep. of Germany

[21] Appl. No.: 665,860

[22] Filed: Mar. 7, 1991

[30] Foreign Application Priority Data

Mar. 7, 1990 [DE] Fed. Rep. of Germany ........ 4007036

[51] Int. Cl.$^5$ .............................................. G01N 21/78
[52] U.S. Cl. ..................... 436/110; 436/166; 436/18
[58] Field of Search ......................................... 436/110

[56] References Cited

U.S. PATENT DOCUMENTS 4,003,706  1/1977  Szekely ............................. 436/110

OTHER PUBLICATIONS

Velghe et al., "Rapid Spectrophotometric Determination of Nitrate in Mineral Waters with Resorcinol," Analyst, vol. 110, pp. 313–314 (Mar. 1985).

Heil, "Entwicklung einer neuen Methode zuf schnellen Bestimmung von Nitrat in Oberflächenwasser, Grundwasser und Trinkwasser," Gewässerschutz, Wasser, Abwasser (GWA), vol. 79, pp. 74–87 (1985).

*Primary Examiner*—James C. Housel
*Assistant Examiner*—David Redding
*Attorney, Agent, or Firm*—Millen, White, Zelano, & Branigan

[57] ABSTRACT

The invention relates to a procedure and agent for the colorimetric determination of nitrate ions in aqueous solutions by mixing the sample which is to be investigated with resorcinol and a mixture of sulfuric acid and phosphoric acid, characterized in that at least 2 g/l, preferably about 10 to 30 g/l chloride ions are also added.

11 Claims, No Drawings

PROCEDURE AND AGENT FOR THE DETERMINATION OF NITRATE IONS

BACKGROUND OF THE INVENTION

The invention relates to a procedure and agent for the colorimetric determination of nitrate ions in aqueous solutions.

The quantitative determination of nitrate ions is becoming of increasing importance in analysis. Nitrate in drinking water and service water, in foodstuffs, in agricultural chemistry and in general environmental analysis is increasingly becoming a general criterion of quality. Reliable and economic determination procedures are required for monitoring the limit values of nitrate in drinking water, for monitoring the fertilizer residues in foodstuffs and for determining the level of nitrate in soils which are used for agriculture in order to accomplish cost-effective mineral fertilizing.

Nitrate determinations are of great importance especially where there is suspicion of excessively high nitrate concentrations which are hazardous to health, in order to be able to prevent, for example, potentially carcinogenic nitrosamine formation.

Both physical and chemical methods for the determination of nitrate are known. The chemical methods are based either on the reduction of the nitrate to nitrite and the detection of the nitrite via the formation of an azo dye or on a nitration of phenolic compounds with the formation of colored aromatic nitro compounds.

On the one hand, carcinogenic reagents (for example hydrazine) or toxic heavy metals, which enter the environment with the sample wastes, are used in the reduction methods, and on the other hand, the methods based on the nitration of phenol derivatives in concentrated sulfuric acid are elaborate and are more or less subject to interference from chloride ions present in the sample.

Analyst 110, 313 (1985) discloses a spectrophotometric method for determining nitrate in mineral waters using resorcinol and concentrated sulfuric acid at 360 nm. The investigations showed that chloride ions have no effect on the analytical result up to a concentration of 500 mg/l; the deviations in the analytical result are +2.5, +6.3 and +9% at 1000, 2000 and 3000 mg/l respectively.

It is stated in Gewasserschutz, Wasser, Abwasser (GWA) 79, 74 (1985) that most of the tested organic amines and phenols and their derivatives proved to be unsuitable for a nitrate assay. In the case of catechol, mixtures of sulfuric acid and phosphoric acid are described as completely unsuitable. There is no interference with the determination using catechol in sulfuric acid by up to 1000 mg/l chloride ions.

SUMMARY OF THE INVENTION

An object of the invention is to provide a straightforward and sensitive procedure and reagent for determining nitrate ions, with which accurate nitrate determinations can be carried out without difficulty even in salt-containing samples.

It has been found, surprisingly, that nitrate determinations yield accurate analytical results even in samples with a high salt content, such as sea water, digestion solutions or in aqueous solutions of soil and plant extracts, when carried out in the presence of a relatively high chloride concentration.

The invention relates to a procedure for the colorimetric determination of nitrate ions by mixing the sample which is to be investigated with resorcinol and a mixture of sulfuric acid and phosphoric acid, which is characterized in that at least about 2 g/l preferably about 10 to 30 g/l chloride ions are added.

The invention also relates to an agent for the colorimetric determination of nitrate ions in a sample, containing resorcinol, sulfuric acid and phosphoric acid, which is characterized by containing at least about 2 g/l preferably about 10 to 30 g/l chloride ions.

The reaction is carried out with resorcinol as color reagent in the presence of a mixture of concentrated mineral acids, preferably in a mixture of 90–95% by volume of 95–97%, more preferably 96% sulfuric acid and 5–10% by volume of 84–86%, more preferably 85% phosphoric acid. A mixture of sulfuric acid and phosphoric acid in the ratio 9:1 by volume has emerged as being particularly suitable. The phosphoric acid leads to colorless blanks and simultaneously acts as a masking agent for iron ions.

The amount of the resorcinol in the mixture can vary within wide limits. The amount suitable for the procedure according to the invention is in the range from about 0.1 to 0.2% by weight of the measurement mixture, preferably from 0.12 to 0.16% by weight. For example, 0.15 to 0.35 ml of a 5% solution may be used. The amount of chloride ions to be employed according to the invention is preferably at least about 2 g/l more preferably from about 10 to 30 g/l.

It has proved expedient to provide the resorcinol and the required amount of chloride in the form of a dry mixture, for example with sodium chloride or else with sodium chloride mixed with other inorganic salts, for example 1:1 sodium chloride/sodium sulfate containing 3 to 8% resorcinol.

The nitrate ion determination is carried out in such a way that the mixture of resorcinol and chloride is homogenized in the mixture of sulfuric acid and phosphoric acid, the sample solution which is to be investigated is added, and mixing is carried out. Preferably, the volume ratio of an aqueous sample solution to the mixture of acids is about 2:1 to 1:0.8, more preferably about 1:1. It is also possible to add first the resorcinol-containing mixture and then the mixture of the acids to the sample solution. The reaction is complete after only a few minutes and can be evaluated either by spectrophotometry at 505 nm or visually by use of color comparison scales. In the presence of nitrate, the reagent gives a blue-red compound. The reaction is very sensitive and makes it possible to determine nitrates, for example even in sea water, in the range 0–15 mg/l when 1 cm measuring cuvettes are used. The measurement range can be shifted upwards or downwards by altering the path length of the cuvettes. The blank is colorless.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 40 07 036.0, filed Mar. 7, 1990, are hereby incorporated by reference.

EXAMPLES

Example 1

160 mg of a 1:1 mixture of sodium chloride and sodium sulfate containing 5% resorcinol are homogenized in 2 ml of a mixture of 96% sulfuric acid and 85% phosphoric acid (9:1 parts by volume). 2 ml of sample solution are pipetted into this mixture and mixed. After the mixture has stood for 15 minutes it is measured in a 1 cm measuring cuvette at 505 nm with a blank sample prepared at the same time as reference. The concentration of nitrate ions is read off, using the measured extinction, from a calibration plot previously constructed with solutions containing nitrate ions of accurately known content.

The amount of the resorcinol-containing mixture can vary within wide limits; thus, the same results are obtained when 120 or 200 mg are employed in place of 160 mg of the mixture.

Example 2

Determination of Nitrate in Sea Water

Water from the North Sea is adjusted with potassium nitrate to concentrations of 5, 10 and 15 mg/l nitrate. Determinations of nitrate in these samples are carried out in analogy to Example 1 using 185 mg of the resorcinol-containing reagent with a blank made with undoped sea water plus reagents as reference for the measurement. The nitrate concentration is established using standard solutions of known concentrations. The measurements on the prepared samples agree exactly with the values on the calibration plot.

Example 3

A nitrate determination is carried out in analogy to Example 1 using 145 mg of the resorcinol-containing mixture. After 15 minutes, the resulting blue-red color of the solution is compared with a color scale or color disc which contains comparison samples of the color for defined nitrate concentrations. This arrangement allows semiquantitative nitrate determination in ranges in which color differences can still be clearly differentiated by eye.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the colorimetric determination of nitrate ions comprising mixing a sample to be investigated with a mixture comprising resorcinol, sulfuric acid, phosphoric acid and at least 2 g/l of chloride ions.

2. A process according to claim 1, wherein the amount of chloride ions is about 10 to 30 g/l.

3. A process according to claim 1, wherein the mixture consists essentially of resorcinol, sulfuric acid, phosphoric acid and chloride ions.

4. A process according to claim 1, wherein the mixture consists of resorcinol, sulfuric acid, phosphoric acid and chloride ions.

5. A process according to claim 1, wherein the determination is carried out in a mixture of 90–95% by volume sulfuric acid and 5–10% by volume phosphoric acid, based on the total mixture volume.

6. A process according to claim 5, wherein the sulfuric acid has a concentration of about 96% and the phosphoric acid has a concentration of about 85%.

7. A process according to claim 1, wherein the volume ratio of sulfuric acid to phosphoric acid is about 9:1.

8. A process according to claim 1, wherein the amount of resorcinol is about 0.1 to 0.2% by weight based on the mixture.

9. A process according to claim 1, wherein the amount of resorcinol is about 0.12–0.16% by weight based on the mixture.

10. An agent for the colorimetric determination of nitrate ions in a sample, containing resorcinol, sulfuric acid and phosphoric acid, and containing at least 2 g/l of chloride ions.

11. An agent according to claim 10, containing about 10 to 30 g/l of chloride ions.

* * * * *